(12) United States Patent
Fujimoto et al.

(10) Patent No.: US 7,834,230 B2
(45) Date of Patent: Nov. 16, 2010

(54) CATALYST AND PROCESS FOR PRODUCING LIQUEFIED PETROLEUM GAS

(75) Inventors: Kaoru Fujimoto, Kitakyushu (JP); Kenji Asami, Kitakyushu (JP); Xiaohong Li, Kitakyushu (JP); Qianwen Zhang, Kitakyushu (JP)

(73) Assignee: Japan Gas Synthesized, Ltd., Tokyo (JP)

( * ) Notice: Subject to any disclaimer, the term of this patent is extended or adjusted under 35 U.S.C. 154(b) by 946 days.

(21) Appl. No.: 11/465,720

(22) Filed: Aug. 18, 2006

(65) Prior Publication Data

US 2007/0106106 A1 May 10, 2007

(30) Foreign Application Priority Data

Nov. 7, 2005 (JP) ............................. 2005-321864

(51) Int. Cl.
C07C 1/04 (2006.01)
C07C 1/10 (2006.01)
C07C 1/207 (2006.01)

(52) U.S. Cl. ..................................... 585/733

(58) Field of Classification Search .................. 585/733
See application file for complete search history.

(56) References Cited

FOREIGN PATENT DOCUMENTS

JP      61-23668      2/1986

OTHER PUBLICATIONS

Kaoru Fujimoto, et al., Selective Synthesis of LPG from Synthesis Gas, The Chemical Society of Japan, Bull. Cem. Soc. Jpn. 58, 3059-3060, Oct. 1985.

O. Yingjie Jin, et al., Methanol/Dimethyl Ether Conversion on Zeolite Catalysts for Indirect Synthesis of LPG from Natural Gas, The summaries of the 92th Catalysis Society of Japan (CATSJ; Meeting, Meeting-A), Sep. 18, 2003.

*Primary Examiner*—Thuan Dinh Dang
(74) *Attorney, Agent, or Firm*—Knobbe Martens Olson & Bear LLP (57) ABSTRACT

A catalyst for producing a liquefied petroleum gas according to the present invention comprises a Pd- and/or Pt-based catalyst component and a USY-type zeolite. By using the catalyst, a hydrocarbon containing propane or butane as a main component, i.e. a liquefied petroleum gas, can be produced with high activity, high selectivity and high yield from at least one of methanol and dimethyl ether.

10 Claims, 1 Drawing Sheet

Fig.1

CATALYST AND PROCESS FOR PRODUCING LIQUEFIED PETROLEUM GAS

TECHNICAL FIELD

This invention relates to a catalyst for producing a liquefied petroleum gas containing propane or butane as a main component by reacting at least one selected from the group consisting of methanol and dimethyl ether with hydrogen. This invention also relates to a process for producing a liquefied petroleum gas using the catalyst.

Furthermore, this invention relates to a process for producing a liquefied petroleum gas containing propane or butane as a main component from a synthesis gas, via methanol and/or dimethyl ether. This invention also relates to a process for producing a liquefied petroleum gas containing propane or butane as a main component from a carbon-containing starting material such as a natural gas, via methanol and/or dimethyl ether.

BACKGROUND OF THE INVENTION

Liquefied petroleum gas (LPG) is a liquefied petroleum-based or natural-gas-based hydrocarbon which is gaseous at an ambient temperature under an atmospheric pressure by compression while optionally cooling, and the main component of it is propane or butane. LPG is advantageously transportable because it can be stored or transported in a liquid form. Thus, in contrast with a natural gas that requires a pipeline for supply, it has a characteristic that it can be filled in a container to be supplied to any place. For that reason, LPG comprising propane as a main component, i.e. propane gas, has been widely used as a fuel for household and business use. At present, propane gas is supplied to about 25 million households (more than 50% of the total households) in Japan. In addition to household and business use, LPG is used as a fuel for a portable product such as a portable gas burner and a disposable lighter (mainly, butane gas), an industrial fuel and an automobile fuel.

Conventionally, LPG has been produced by 1) collection from a wet natural gas, 2) collection from a stabilization (vapor-pressure regulating) process of crude petroleum, 3) separation and extraction of a product in, for example, a petroleum refining process, or the like.

LPG, in particular propane gas used as a household/business fuel, can be expected to be in great demand in the future. Thus, it may be very useful to establish an industrially practicable and new process for producing LPG.

As a process for producing LPG, Japanese Patent Laid-open Publication No. 61-23688 discloses that a synthesis gas consisting of hydrogen and carbon monoxide is reacted in the presence of a mixed catalyst obtained by physically mixing a methanol synthesis catalyst, specifically a $CuO$—$ZnO$—$Al_2O_3$ catalyst or a $Pd/SiO_2$ catalyst, with a methanol conversion catalyst composed of a zeolite having an average pore size of about 10 Å (1 nm) or more, specifically a Y-type zeolite, to give a liquefied petroleum gas or a mixture of hydrocarbons similar in composition to LPG.

However, the above-mentioned process does not always give a sufficiently high activity (a conversion of carbon monoxide), a sufficiently high yield of a hydrocarbon, and a sufficiently high yield of propane and butane. A yield of hydrocarbon is at most 36.0%, while a yield of propane and butane is about 26%. In another case, a yield of hydrocarbon is 35.7%, while a yield of propane and butane is about 27%.

Furthermore, a product obtained by the above-mentioned process may not have a sufficiently low carbon dioxide content. When a yield of hydrocarbon is at its highest, that is 36.0%, a yield of carbon dioxide is 33.9%. When a yield of hydrocarbon is 35.7%, a yield of carbon dioxide is 30.7%. Carbon dioxide is less useful and is hard to be reused, and therefore, it is economically undesirable to yield a large amount of carbon dioxide as a by-product.

As a process for producing LPG, "Selective Synthesis of LPG from Synthesis Gas", Kaoru Fujimoto et al., Bull. Chem. Soc. Jpn., 58, p. 3059-3060 (1985) discloses that, using a hybrid catalyst consisting of a methanol synthesis catalyst such as a 4 wt % $Pd/SiO_2$, a Cu—Zn—Al mixed oxide {Cu:Zn:Al=40:23:37 (atomic ratio)} or a Cu-based low-pressure methanol synthesis catalyst (Trade name: BASF S3-85) and a high-silica Y-type zeolite with $SiO_2/Al_2O_3$=7.6 treated with steam at 450° C. for 1 hour, C2 to C4 paraffins can be produced in a selectivity of 69 to 85% via methanol and dimethyl ether from a synthesis gas. However, as is in the process described in the above-mentioned Japanese Patent Laid-open Publication No. 61-23688, this process does not always give a sufficiently high activity (a conversion of carbon monoxide) and a sufficiently high yield of a hydrocarbon, and the obtained product may not have a sufficiently low carbon dioxide content.

On the other hand, "Methanol/Dimethyl Ether Conversion on Zeolite Catalysts for Indirect Synthesis of LPG from Natural Gas", Yingjie Jin et al., Dai 92 Kai Shokubai Touronkai Touronkai A Yokousyuu, (the summaries of the 92th Catalysis Society of Japan (CatSJ) Meeting, Meeting-A), p. 322, Sep. 18, 2003 discloses a process for producing LPG, using at least one selected from the group consisting of methanol and dimethyl ether as a starting material. Specifically, a starting gas, whose composition is methanol:$H_2$:$N_2$=1:1:1, was passed through the two-layered catalyst layer consisting of ZSM-5 as the former layer and Pt—C as the latter layer (ZSM-5/Pt—C Series) or a mixed catalyst layer consisting of ZSM-5 and Pt—C (ZSM-5/Pt—C Pellet-mixture), under a slightly increased pressure, at a reaction temperature of 603 K (330° C.) and at a methanol-based LHSV of 20 $h^{-1}$, whereby carrying out an LPG production reaction.

However, the above-mentioned process may not give a sufficiently high conversion of methanol to propane and butane. When using a ZSM-5/Pt—C Series as a catalyst layer, a conversion of methanol to a hydrocarbon is 64.0% on the basis of carbon, while a conversion of methanol to propane and butane is about 38.7% on the basis of carbon. When using a ZSM-5/Pt—C Pellet-mixture as a catalyst layer, the result is even worse; specifically, a conversion of methanol to a hydrocarbon is 20.6% on the basis of carbon, while a conversion of methanol to propane and butane is about 10.8% on the basis of carbon.

Furthermore, when using a ZSM-5/Pt—C Series as a catalyst layer, the deterioration with time of the catalyst may be generally significant and the catalyst life may not be sufficiently long. Generally, when an olefin is produced from methanol and/or dimethyl ether using a zeolite as a catalyst, the zeolite catalyst is apt to be deteriorated due to coking.

SUMMARY OF THE INVENTION

An objective of this invention is to provide a catalyst for producing a hydrocarbon containing propane or butane as a main component, i.e. a liquefied petroleum gas (LPG), with high activity, high selectivity and high yield, from at least one selected from the group consisting of methanol and dimethyl ether.

Another objective of this invention is to provide a process for economically producing a liquefied petroleum gas (LPG)

with a high yield, from at least one selected from the group consisting of methanol and dimethyl ether, using the above catalyst.

The present invention provides a catalyst for producing a liquefied petroleum gas, which is used for producing a liquefied petroleum gas containing propane or butane as a main component by reacting at least one selected from the group consisting of methanol and dimethyl ether with hydrogen, comprising a Pd- and/or Pt-based catalyst component in which Pd and/or Pt is supported on a support; and a USY-type zeolite.

The present invention also provides a process for producing a liquefied petroleum gas, comprising a step of:

reacting at least one selected from the group consisting of methanol and dimethyl ether with hydrogen in the presence of the above catalyst, whereby producing a liquefied petroleum gas containing propane or butane as a main component.

Furthermore, the present invention provides a process for producing a liquefied petroleum gas, comprising:

(1) a step of producing methanol wherein a synthesis gas is passed through a catalyst layer comprising a methanol synthesis catalyst, whereby producing a reactant gas containing methanol and hydrogen; and (2) a step of producing a liquefied petroleum gas wherein the reactant gas produced in the step of producing methanol is passed through a catalyst layer comprising the above catalyst, whereby producing a liquefied petroleum gas containing propane or butane as a main component.

And, the present invention also provides a process for producing a liquefied petroleum gas, comprising:

(1) a step of producing dimethyl ether wherein a synthesis gas is passed through a catalyst layer comprising a methanol synthesis catalyst and a methanol dehydration catalyst, whereby producing a reactant gas containing dimethyl ether and hydrogen; and (2) a step of producing a liquefied petroleum gas wherein the reactant gas produced in the step of producing dimethyl ether is passed through a catalyst layer comprising the above catalyst, whereby producing a liquefied petroleum gas containing propane or butane as a main component.

Furthermore, the present invention provides a process for producing a liquefied petroleum gas, comprising:

(1) a step of producing a synthesis gas from a carbon-containing starting material and at least one selected from the group consisting of $H_2O$, $O_2$ and $CO_2$;

(2) a step of producing methanol wherein the synthesis gas is passed through a catalyst layer comprising a methanol synthesis catalyst, whereby producing a reactant gas containing methanol and hydrogen; and (3) a step of producing a liquefied petroleum gas wherein the reactant gas produced in the step of producing methanol is passed through a catalyst layer comprising the above catalyst, whereby producing a liquefied petroleum gas containing propane or butane as a main component.

And, the present invention also provides a process for producing a liquefied petroleum gas, comprising:

(1) a step of producing a synthesis gas from a carbon-containing starting material and at least one selected from the group consisting of $H_2O$, $O_2$ and $CO_2$;

(2) a step of producing dimethyl ether wherein the synthesis gas is passed through a catalyst layer comprising a methanol synthesis catalyst and a methanol dehydration catalyst, whereby producing a reactant gas containing dimethyl ether and hydrogen; and (3) a step of producing a liquefied petroleum gas wherein the reactant gas produced in the step of producing dimethyl ether is passed through a catalyst layer comprising the above catalyst, whereby producing a liquefied petroleum gas containing propane or butane as a main component.

Herein, the term "synthesis gas" refers to a mixed gas comprising hydrogen and carbon monoxide, and is not limited to a mixed gas consisting of hydrogen and carbon monoxide. A synthesis gas may comprise, for example, carbon dioxide, water, methane, ethane, ethylene and the like. A synthesis gas produced by reforming a natural gas generally contains, in addition to hydrogen and carbon monoxide, carbon dioxide and water vapor. A synthesis gas may be a coal gas produced by coal gasification or a water gas produced from a coal coke.

A catalyst for producing a liquefied petroleum gas according to this invention comprises a Pd- and/or Pt-based catalyst component in which Pd and/or Pt is supported on a support, and a USY-type zeolite. Examples of a Pd- and/or Pt-based catalyst component include $Pd/SiO_2$ and $Pt/SiO_2$. By reacting at least one selected from the group consisting of methanol and dimethyl ether with hydrogen in the presence of the catalyst according to this invention, a hydrocarbon containing propane or butane as a main component, i.e. a liquefied petroleum gas (LPG) can be produced with high activity, high selectivity and high yield. Particularly, according to this invention, the decomposition of methanol and/or dimethyl ether to CO and $CO_2$ may be inhibited and therefore, the production amount of carbon monoxide and carbon dioxide as by-products may be significantly reduced, while keeping the conversion of methanol and/or dimethyl ether high.

In this invention, LPG containing propane or butane as a main component may be produced from at least one selected from the group consisting of methanol and dimethyl ether, and hydrogen, in accordance with the following formula (I).

In this invention, methanol is dehydrated to generate a carbene ($H_2C$:) by a concerted catalysis of an acidic site and a basic site, which are at a spatial field inside a pore in a USY-type zeolite. And then, the carbene is polymerized to form an olefin containing propylene or butene as a main component. More specifically, it may be thought that ethylene is formed as a dimer; propylene is formed as a trimer or a reaction product with ethylene; and butylene is formed as a tetramer, a reaction product with propylene or a product of dimerization of ethylene.

In the olefin formation process, there would occur other reactions such as formation of dimethyl ether by dehydration-dimerization of methanol and formation of methanol by hydration of dimethyl ether.

And then, the formed olefin is hydrogenated mainly by the catalysis of a Pd- and/or Pt-based catalyst component, to form a paraffin containing propane or butane as a main component, i.e. LPG.

According to this invention, for example, a hydrocarbon with the total content of propane and butane of 55% or more, specifically 60% or more on the basis of carbon can be produced with high activity and high selectivity, specifically a conversion of methanol and/or dimethyl ether to a hydrocarbon of 90% or more, more specifically 95% or more.

According to this invention, LPG can be produced with a conversion of methanol and/or dimethyl ether to propane and butane of 55% or higher, specifically 60% or higher on the basis of carbon. Furthermore, according to this invention, a conversion of methanol and/or dimethyl ether to carbon monoxide and carbon dioxide can be reduced to 6% or less, particularly 4% or less on the basis of carbon.

When reacting at least one selected from the group consisting of methanol and dimethyl ether with hydrogen to produce a liquefied petroleum gas, a product generally includes, in addition to propane and butane as main components, other hydrocarbons such as ethane, methane, pentane and hexane. These hydrocarbons other than propane and butane are by-products in an LPG production reaction, but they are more useful than carbon monoxide and carbon dioxide. The hydrocarbons other than propane and butane can be used as, for example, a calorie adjustor for town gas, a chemical raw material, a gasoline fuel and the like. Moreover, methanol, which is used as a starting material in this invention, is industrially produced on a large scale from a synthesis gas, and the hydrocarbons other than propane and butane can be used as a starting material for producing the synthesis gas. It is economically advantageous to yield a small amount of carbon monoxide and carbon dioxide as a by-product.

In the synthesis reaction of an olefin from methanol and/or dimethyl ether, a zeolite catalyst is apt to be deteriorated due to coking, and therefore, may not have a sufficiently long catalyst life. In contrast, according to the process for producing LPG of this invention, even when using a zeolite-containing catalyst, deterioration of a zeolite due to coking can be prevented and thus LPG can be stably produced for a long period with reducing a catalyst cost.

Furthermore, in a hydrogenation reaction of an olefin, carbon monoxide and carbon dioxide may act as a catalyst poisoning component, and the formation of methane by hydrogenation may occur. Therefore, a gas containing carbon monoxide and/or carbon dioxide is not preferable as a starting gas (a gas fed into a reactor). In contrast, in the process for producing LPG of this invention, the presence of carbon monoxide and/or carbon dioxide in a starting gas has no effect on LPG production.

Methanol, which is a reaction raw material, is industrially produced on a large scale from a synthesis gas, and the product of the methanol synthesis reaction generally contains carbon monoxide, which is an unreacted starting material, and carbon dioxide, which is a by-product. Dimethyl ether can be also produced from a synthesis gas, and the product of the dimethyl ether synthesis reaction also generally contains carbon monoxide and/or carbon dioxide. When constructing a process comprising the step of producing methanol and/or dimethyl ether from a synthesis gas and the following step of producing LPG from methanol and/or dimethyl ether, employing the process for producing LPG of this invention may be economically advantageous, because it is not necessary to purify a product after methanol and/or dimethyl ether synthesis reaction, and thus the product can be used as a starting material for producing LPG without any treatment.

As described above, according to this invention, a hydrocarbon containing propane or butane as a main component, i.e. a liquefied petroleum gas (LPG), can be economically produced with a relatively higher yield from at least one selected from the group consisting of methanol and dimethyl ether, or from a synthesis gas.

DESCRIPTION OF THE MAIN SYMBOLS

11: a reactor
11a: a catalyst layer containing a catalyst for producing a liquefied petroleum gas
12, 13: lines.

DETAILED DESCRIPTION OF THE EMBODIMENTS

1. Catalyst for Producing a Liquefied Petroleum Gas According to the Present Invention A catalyst for producing a liquefied petroleum gas according to the present invention comprises a Pd- and/or Pt-based catalyst component in which Pd and/or Pt is supported on a support, and a USY-type zeolite. A catalyst for producing a liquefied petroleum gas of this invention can comprise other additive components as long as its intended effect would not be impaired.

A ratio of the Pd- and/or Pt-based catalyst component to the USY-type zeolite (Pd- and/or Pt-based catalyst component/USY-type zeolite; by weight) is preferably 0.1 or more, more preferably 0.3 or more. By adjusting a ratio of the Pd- and/or Pt-based catalyst component to the USY-type zeolite (Pd- and/or Pt-based catalyst component/USY-type zeolite; by weight) to 0.1 or more, a higher yield of propane and butane can be achieved.

A ratio of the Pd- and/or Pt-based catalyst component to the USY-type zeolite (Pd- and/or Pt-based catalyst component/USY-type zeolite; by weight) is preferably 1.5 or less, more preferably 1.2 or less, particularly preferably 0.8 or less. By adjusting a ratio of the Pd- and/or Pt-based catalyst component to the USY-type zeolite (Pd- and/or Pt-based catalyst component/USY-type zeolite; by weight) to 1.5 or less, a higher yield of propane and butane can be achieved, and furthermore the production amount of carbon monoxide, carbon dioxide and methane as by-products can be more sufficiently reduced. By adjusting a ratio of the Pd- and/or Pt-based catalyst component to the USY-type zeolite (Pd- and/or Pt-based catalyst component/USY-type zeolite; by weight) to 0.8 or less, a further higher yield of propane and butane can be achieved, and the production amount of heavy hydrocarbons (C5 or more) as by-products can be more sufficiently reduced.

By adjusting a ratio of the Pd- and/or Pt-based catalyst component to the USY-type zeolite within the above range, propane and/or butane can be produced with a higher selectivity and a higher yield.

A ratio of the Pd- and/or Pt-based catalyst component to the USY-type zeolite is not limited to the above range, and can be appropriately determined, depending on the amount of Pd and/or Pt in the Pd- and/or Pt-based catalyst component, and the like.

(Pd- and/or Pt-Based Catalyst Component)

A Pd- and/or Pt-based catalyst component is Pd and/or Pt supported on a support. In the light of catalytic activity, Pd and/or Pt is preferably supported on a support in a highly dispersed manner.

Pd and/or Pt may not be necessarily contained as a metal, but can be contained in the form of an oxide, a nitrate, a chloride or the like. In such a case, for achieving higher catalytic activity, the catalyst can be preferably subjected to, for example, reduction by hydrogen before the reaction, to convert Pd and/or Pt in the Pd- and/or Pt-based catalyst component into metallic palladium and/or metallic platinum.

The amount of supported Pd and/or Pt in a Pd- and/or Pt-based catalyst component is preferably 0.1 wt % or more, more preferably 0.3 wt % or more. In the light of dispersibility and economical efficiency, the amount of supported Pd and/or Pt in a Pd- and/or Pt-based catalyst component is preferably 5 wt % or less, more preferably 3 wt % or less. By adjusting the amount of supported Pd and/or Pt in a Pd- and/or Pt-based catalyst component within the above range, propane and/or butane can be produced with a higher conversion, a higher selectivity and a higher yield.

A support for Pd- and/or Pt-based catalyst component may be selected from known supports without limitation. Examples of a support include silica (silicon dioxide), alumina, silica-alumina, carbon (activated charcoal); and oxides of zirconium, titanium, cerium, lanthanum, iron or the like, and composite oxides containing two or more types of these metals, and composite oxides containing one or more types of these metals and one or more types of other metals. Such supports may be used alone or in combination of two or more.

Among others, a preferable support for Pd- and/or Pt-based catalyst component is silica. By using silica as a support, propane and/or butane can be produced with a higher selectivity and a higher yield without producing carbon dioxide as a by-product.

A silica support preferably has a specific surface area of 450 $M^2/g$ or more, more preferably 500 $m^2/g$ or more. By using a silica support having a specific surface area within the above range, higher catalytic activity can be achieved and propane and/or butane can be produced with a higher conversion and a higher yield.

The upper limit of a specific surface area of a silica support is not particularly restricted, but is generally about 1000 $m^2/g$.

A specific surface area of silica can be determined, for example, by a BET method using $N_2$ as an adsorption gas and a fully automatic measuring apparatus for specific surface area and pore distribution (e.g., ASAP2010, Shimadzu Corporation).

In this invention, a Pd- and/or Pt-based catalyst component may be a silica support on which other components, in addition to Pd and Pt, are supported as long as the desired effects of the catalyst are maintained.

(USY-Type Zeolite)

A USY-type zeolite used in this invention may be selected from USY-type zeolites containing a metal such as alkali metals, alkaline earth metals and transition metals; USY-type zeolites ion-exchanged with these metals or the like; and USY-type zeolites on which these metals or the like are supported. But a preferable USY-type zeolite is a proton-type zeolite. By using a proton-type USY-type zeolite having a suitable acid strength and a suitable acidity (acid concentration), higher catalytic activity can be achieved, and propane and/or butane can be produced with a higher conversion and a higher selectivity.

A $SiO_2/Al_2O_3$ ratio of a USY-type zeolite is more preferably 5 or more, particularly preferably 15 or more. By using a USY-type zeolite with a $SiO_2/Al_2O_3$ ratio of 5 or more, particularly preferably 15 or more, the production amount of carbon monoxide and carbon dioxide as by-products can be more sufficiently reduced, and a higher selectivity of propane and butane can be achieved.

And, a $SiO_2/Al_2O_3$ ratio of a USY-type zeolite is more preferably 50 or less, particularly preferably 40 or less, further preferably 25 or less. By using a USY-type zeolite with a $SiO_2/Al_2O_3$ ratio of 50 or less, further preferably 25 or less, a higher conversion of methanol and/or dimethyl ether can be achieved, and the production amount of methane as by-products can be more sufficiently reduced, and a higher selectivity of propane and butane can be achieved.

(Process for Producing a Catalyst According to the Present Invention)

A catalyst for producing a liquefied petroleum gas according to this invention is preferably produced by separately preparing a Pd- and/or Pt-based catalyst component and a USY-type zeolite, and then mixing them. By separately preparing a Pd- and/or Pt-based catalyst component and a USY-type zeolite, a composition, a structure and a property of each component can be easily optimized for each function.

A Pd- and/or Pt-based catalyst component, in which Pd and/or Pt is supported on a support (e.g. silica), can be prepared by a known method such as an impregnation method and a precipitation method.

A USY-type zeolite can be prepared by a known method, and a commercially available product can be used.

Some of Pd- and/or Pt-based catalyst components must be activated by reduction treatment before use, including those containing Pd and/or Pt as an oxide, nitrate or chloride. In this invention, it is not necessarily required to activate a Pd- and/or Pt-based catalyst component by reduction treatment in advance. The Pd- and/or Pt-based catalyst component can be activated by reduction treatment of the catalyst for producing a liquefied petroleum gas of this invention, before the beginning of the reaction, after producing the catalyst by mixing a Pd- and/or Pt-based catalyst component and a USY-type zeolite, and then molding the mixture.

The conditions of the reduction treatment can be determined, depending on some factors such as the type of the Pd- and/or Pt-based catalyst component, as appropriate.

A catalyst for producing a liquefied petroleum gas according to the present invention can be produced by homogeneously mixing a Pd- and/or Pt-based catalyst component and a USY-type zeolite, and then, if necessary, molding the mixture. A procedure of mixing and molding these catalyst components is not particularly limited, but is preferably a dry method. When mixing and molding these catalyst components by a wet method, there may occur a compound transfer between these catalyst components, for example, neutralization due to transfer of a basic component in a Pd- and/or Pt-based catalyst component to an acidic site in a USY-type zeolite, leading to the change of a property optimized for each function of these catalyst components, and the like. A catalyst can be molded by an appropriate method such as an extrusion molding and a tablet-compression molding.

In this invention, a Pd- and/or Pt-based catalyst component and a USY-type zeolite to be mixed preferably have an average particle size of 0.1 μm or more and 5 μm or less. Average particle sizes of a Pd- and/or Pt-based catalyst component and a USY-type zeolite to be mixed are more preferably 0.5 μm or more and 2 μm or less. By mixing a Pd- and/or Pt-based catalyst component and a USY-type zeolite having an average particle size within the above range, a higher conversion of methanol and/or dimethyl ether can be achieved, and a higher selectivity of propane and butane can be achieved.

It is preferable that a Pd- and/or Pt-based catalyst component and a USY-type zeolite to be mixed have the same average particle size.

2. Process for Producing a Liquefied Petroleum Gas

Next, there will be described a process for producing a liquefied petroleum gas comprising propane or butane, preferably propane, as a main component, by reacting at least one selected from the group consisting of methanol and dimethyl ether with hydrogen using at least one of the catalysts as described above.

In the process for producing LPG according to this invention, a reaction raw material may be methanol or dimethyl ether alone, or may be a mixture of methanol and dimethyl ether. When using a mixture of methanol and dimethyl ether as a reaction raw material, a ratio of methanol to dimethyl ether is not particularly limited, and can be appropriately determined.

The reaction can be conducted in a fixed bed, a fluidized bed or a moving bed. The reaction conditions such as a composition of a starting gas, a reaction temperature, a reaction pressure and a contact time with a catalyst can be appropriately determined. For example, the LPG production reaction may be carried out under the following conditions.

In the light of achieving a higher catalytic activity, a reaction temperature is preferably 350° C. or higher, more preferably 360° C. or higher, particularly preferably 400° C. or higher. In the light of achieving a higher selectivity for a hydrocarbon and a higher selectivity for propane and butane, as well as a long catalyst life, a reaction temperature is preferably 470° C. or lower, more preferably 450° C. or lower.

In the light of achieving a higher activity and good operability of an apparatus, a reaction pressure is preferably 0.3 MPa or higher, more preferably 0.4 MPa or higher. Furthermore, when a reaction pressure is 0.8 MPa or higher, more preferably 1 MPa or higher, a higher selectivity for propane and butane can be achieved. In the light of economical efficiency and safety, a reaction pressure is preferably 3 MPa or lower, more preferably 2.5 MPa or lower.

A gas space velocity is preferably 1500 $hr^{-1}$ or more, more preferably 1800 $hr^{-1}$ or more, in the light of economical efficiency. In addition, a gas space velocity is preferably 10000 $hr^{-1}$ or less, more preferably 5000 $hr^{-1}$ or less, in the light of achieving a higher activity and a higher selectivity for propane and butane.

When a reaction raw material is methanol, a concentration of methanol in a gas fed into a reactor (also referred to as a "starting gas") is preferably 20 mol % or more, more preferably 30 mol % or more, in the light of productivity and economical efficiency. In the light of reducing a calorific value and a deterioration of a catalyst, a concentration of methanol in a gas fed into a reactor is preferably 60 mol % or less, more preferably 40 mol % or less.

When a reaction raw material is methanol, a concentration of hydrogen in a gas fed into a reactor is preferably 1 mole or more, more preferably 1.2 moles or more per 1 mole of methanol, in the light of improving a hydrogenation rate and reducing deterioration of a catalyst. In the light of productivity and economical efficiency, a concentration of hydrogen in a gas fed into a reactor is preferably 3 moles or less, more preferably 2 moles or less per 1 mole of methanol.

When a reaction raw material is dimethyl ether, a concentration of dimethyl ether in a gas fed into a reactor is preferably 10 mol % or more, more preferably 20 mol % or more, in the light of productivity and economical efficiency. In the light of reducing a calorific value and a deterioration of a catalyst, a concentration of dimethyl ether in a gas fed into a reactor is preferably 40 mol % or less, more preferably 30 mol % or less.

When a reaction raw material is dimethyl ether, a concentration of hydrogen in a gas fed into a reactor is preferably 2 mole or more, more preferably 2.5 moles or more per 1 mole of dimethyl ether, in the light of improving a hydrogenation rate and reducing deterioration of a catalyst. In the light of productivity and economical efficiency, a concentration of hydrogen in a gas fed into a reactor is preferably 5 moles or less, more preferably 4 moles or less per 1 mole of dimethyl ether.

When a reaction raw material is a mixture of methanol and dimethyl ether, concentrations of methanol, dimethyl ether and hydrogen in a gas fed into a reactor are preferably within the same range as the above preferable range when a reaction raw material is methanol and the above preferable range when a reaction raw material is dimethyl ether. And, these preferable ranges can be calculated based on a ratio of methanol to dimethyl ether.

A gas fed into a reactor may contain water, an inert gas and the like, in addition to at least one of methanol and dimethyl ether, which are reaction raw materials, and hydrogen. The gas fed into a reactor may contain carbon monoxide and/or carbon dioxide.

At least one of methanol and dimethyl ether, and hydrogen may be mixed, and then fed into a reactor or, alternatively, these may be fed into a reactor separately.

A starting gas can be dividedly fed into the reactor so as to control a reaction temperature.

The reaction can be conducted in a fixed bed, a fluidized bed, a moving bed or the like, and can be preferably selected, taking both of control of a reaction temperature and a regeneration method of the catalyst into account. For example, a fixed bed may include a quench type reactor such as an internal multistage quench type, a multitubular type reactor, a multistage type reactor having a plurality of internal heat exchangers or the like, a multistage cooling radial flow type, a double pipe heat exchange type, an internal cooling coil type, a mixed flow type, and other types of reactors.

When used, a catalyst for producing a liquefied petroleum gas can be diluted with silica, alumina or an inert and stable heat conductor for controlling a temperature. In addition, when used, a catalyst for producing a liquefied petroleum gas can be applied to the surface of a heat exchanger for controlling a temperature.

According to the present invention, an LPG production reaction can be carried out with a conversion of methanol and/or dimethyl ether of 99% or more, particularly about 100%. Furthermore, according to the present invention, an LPG production reaction can be carried out with such a high activity and selectivity that a conversion of methanol and/or dimethyl ether to a hydrocarbon is 90% or more, particularly 95% or more.

A reaction product gas thus produced (a lower-paraffin-containing gas) comprises a hydrocarbon containing propane or butane as a main component. In the light of liquefaction properties, it is preferable that the total content of propane and butane is higher in a lower-paraffin-containing gas. According to this invention, there can be obtained a lower-paraffin-containing gas having a total content of propane and butane of 55% or more, preferably 60% or more on the basis of carbon to the hydrocarbon contained therein.

Furthermore, a lower-paraffin-containing gas produced preferably contains more propane in comparison with butane, in the light of inflammability and vapor pressure properties.

A lower-paraffin-containing gas produced generally comprises water; a low-boiling component having a lower boiling point or a lower sublimation point than the boiling point of propane; and a high-boiling component having a higher boiling point than the boiling point of butane. Examples of a low-boiling component include hydrogen, which is an unreacted starting material; and ethane, methane, carbon monoxide and carbon dioxide, which are by-products. Examples of a high-boiling component include high-boiling paraffins (e.g. pentane, hexane and the like), which are by-products.

Thus, water, a low-boiling component and a high-boiling component are, as necessary, separated from a lower-paraffin-containing gas produced, so as to obtain a liquefied petroleum gas (LPG) comprising propane or butane as a main component. If necessary, methanol and/or dimethyl ether, which are unreacted starting materials, are also separated from a lower-paraffin-containing gas by a known method.

Separation of water, a low-boiling component or a high-boiling component can be conducted in accordance with a known method.

Water can be separated by, for example, liquid-liquid separation.

A low-boiling component can be separated by, for example, gas-liquid separation, absorption separation or distillation; more specifically, gas-liquid separation at an ambient temperature under increased pressure, absorption separation at an ambient temperature under increased pressure, gas-liquid separation with cooling, absorption separation with cooling, or combination thereof. Alternatively, for this purpose, membrane separation or adsorption separation can be conducted, or these in combination with gas-liquid separation, absorption separation or distillation can be conducted. A gas recovery process commonly employed in an oil factory (described in "Oil Refining Processes", ed. The Japan Petroleum Institute, Kodansha Scientific, 1998, pp. 28-32) can be applied to separation of a low-boiling component.

A preferable method of separation of a low-boiling component is an absorption process where a liquefied petroleum gas comprising propane or butane as a main component is absorbed into an absorbent liquid such as a high-boiling paraffin gas having a higher boiling point than butane, and a gasoline.

A high-boiling component can be separated by, for example, gas-liquid separation, absorption separation or distillation.

The conditions of separation may be determined as appropriate in accordance with a known method.

If necessary, the gas may be pressurized and/or cooled so as to obtain a liquefied petroleum gas.

For consumer use, it is preferable that a content of a low-boiling component in the LPG is reduced to 5 mol % or less (including 0 mol %) by separation, for example, in the light of safety in use.

The total content of propane and butane in the LPG thus produced may be 90% or more, more preferably 95% or more (including 100%) on the basis of carbon. And a content of propane in the LPG produced may be 50% or more, more preferably 60% or more, particularly preferably 65% or more (including 100%) on the basis of carbon. Thus, according to this invention, LPG having a composition suitable for a propane gas, which is widely used as a fuel for household and business use, can be produced.

Next, there will be described an embodiment of a process for producing LPG according to this invention with reference to the drawing.

Figure 1:
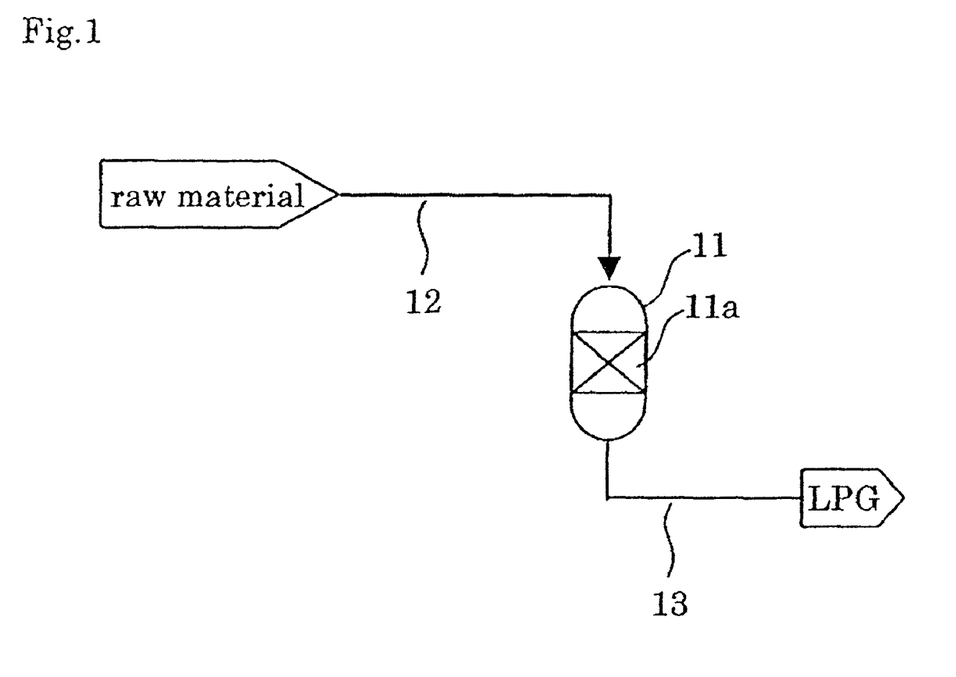
FIG. 1 is a process flow diagram showing a main configuration in an example of an LPG producing apparatus suitable for conducting the process for LPG production according to this invention.

FIG. 1 shows an embodiment of an LPG production apparatus suitable for carrying out a production process for LPG according to this invention.

First, methanol and/or dimethyl ether, which are reaction raw materials, and hydrogen are fed into a reactor 11 via a line 12. In the reactor 11, there is a catalyst layer 11a comprising a catalyst for producing a liquefied petroleum gas according to this invention. In the reactor 11, a hydrocarbon gas containing propane or butane as a main component (a lower-paraffin-containing gas) is produced from methanol and/or dimethyl ether and hydrogen in the presence of the catalyst for producing a liquefied petroleum gas.

The hydrocarbon gas thus produced is pressurized and cooled, after optional removal of water or the like, and LPG, which is a product, is obtained from a line 13. Optionally, hydrogen and the like may be removed from the LPG by, for example, gas-liquid separation.

The LPG production apparatus may be, as necessary, provided with a booster, a heat exchanger, a valve, an instrumentation controller and so on, which are not shown.

Thus, according to this invention, LPG is produced from at least one of methanol and dimethyl ether.

3. Process for Producing a Liquefied Petroleum Gas From a Carbon-Containing Starting Material At present, methanol and dimethyl ether, which are used as a starting material in this invention, are produced in an industrial scale.

Methanol is produced, for example, as follows.

First, a synthesis gas is produced by reacting a natural gas (methane) with at least one selected from the group consisting of $H_2O$, $O_2$ and $CO_2$ in the presence of a reforming catalyst such as an Ni-based catalyst, if necessary, after removing a catalyst poisoning component such as sulfur and a sulfur compound from a natural gas (devulcanization and the like). A water-vapor reforming method, a complex reforming method and an autothermal reforming method of a natural gas (methane) are well known as a process for producing a synthesis gas.

And, a synthesis gas may be also produced by reacting a carbon-containing starting material other than a natural gas with at least one selected from the group consisting of $H_2O$, $O_2$ and $CO_2$, in accordance with a known method. Any carbon-containing substance which can react with at least one selected from the group consisting of $H_2O$, $O_2$ and $CO_2$ to form $H_2$ and CO, can be used as a carbon-containing starting material. For example, a lower hydrocarbon such as ethane, naphtha, a coal, and the like can be used as a carbon-containing starting material.

Next, methanol is produced from the synthesis gas by reacting carbon monoxide with hydrogen in the presence of a methanol synthesis catalyst. When using a Cu—Zn-based catalyst (a composite oxide containing Cu and Zn) such as a Cu—Zn—Al composite oxide and a Cu—Zn—Cr composite oxide as a methanol synthesis catalyst, the reaction is generally carried out at a reaction temperature of about 230 to 300° C. and under a reaction pressure of about 2 to 10 MPa. When using a Zn—Cr-based catalyst (a composite oxide containing Zn and Cr) as a methanol synthesis catalyst, the reaction is generally carried out at a reaction temperature of about 250 to 400° C. and under a reaction pressure of about 10 to 60 MPa.

A product thus produced (crude methanol) generally comprises water; carbon monoxide, which is an unreacted starting material; carbon dioxide and dimethyl ether, which are by-products; and the like. In this invention, the crude methanol can be used as a starting material.

Dimethyl ether is produced by, for example, dehydration reaction of methanol using a solid acid catalyst such as aluminum phosphate.

A process for producing dimethyl ether from a synthesis gas directly, not via methanol, is being put to practical use. In the process, dimethyl ether can be produced by reacting carbon monoxide with hydrogen at a reaction temperature of about 230 to 280° C. and under a reaction pressure of about 3 to 7 MPa in the presence of a mixed catalyst of a methanol synthesis catalyst and a methanol dehydration catalyst, for example, a mixed catalyst comprising a methanol synthesis catalyst and a methanol dehydration catalyst in a ratio of the methanol synthesis catalyst the methanol dehydration catalyst=1:2 to 2:1 (by weight), using a slurry phase reactor.

A product thus produced (crude dimethyl ether) generally comprises water; carbon monoxide, which is an unreacted starting material; carbon dioxide and methanol, which are by-products; and the like. In this invention, the crude dimethyl ether can be used as a starting material.

According to this invention, a liquefied petroleum gas can be produced by producing a synthesis gas from a carbon-containing starting material and at least one selected from the group consisting of $H_2O$, $O_2$ and $CO_2$ (synthesis gas production step); feeding the obtained synthesis gas to a catalyst layer comprising a methanol synthesis catalyst, to produce a reactant gas containing methanol and hydrogen (methanol production step); and feeding the reactant gas produced in the methanol production step to a catalyst layer comprising a catalyst for producing a liquefied petroleum gas, to produce a liquefied petroleum gas containing propane or butane as a main component in accordance with the above process (liquefied petroleum gas production step).

Moreover, according to this invention, a liquefied petroleum gas can be produced by producing a synthesis gas from a carbon-containing starting material and at least one selected from the group consisting of $H_2O$, $O_2$ and $CO_2$ (synthesis gas production step); feeding the obtained synthesis gas to a catalyst layer comprising a methanol synthesis catalyst and a methanol dehydration catalyst, to produce a reactant gas containing dimethyl ether and hydrogen (dimethyl ether production step); and feeding the reactant gas produced in the dimethyl ether production step to a catalyst layer comprising a catalyst for producing a liquefied petroleum gas, to produce a liquefied petroleum gas containing propane or butane as a main component in accordance with the above process (liquefied petroleum gas production step).

A synthesis gas can be produced in accordance with a known method including the method described above. Methanol and dimethyl ether can be also produced in accordance with a known method including the method described above.

In the above process for producing LPG, a shift reactor may be placed downstream of a reformer, which is a reactor for producing a synthesis gas, so that a synthesis gas composition can be adjusted by a shift reaction ($CO+H_2O \rightarrow CO_2+H_2$).

In the above process for producing LPG, a low-boiling component separated from the lower-paraffin-containing gas in the liquefied petroleum gas production step can be recycled as a starting material for the synthesis gas production step.

The whole low-boiling components separated from the lower-paraffin-containing gas can be recycled to the synthesis gas production step. Alternatively, part of the low-boiling components may be removed outside the system, while the rest of low-boiling components may be recycled to the synthesis gas production step. Low-boiling components can be recycled to the synthesis gas production step after separating only desired components.

In this case, in the synthesis gas production step, a content of a low-boiling component in a gas fed into a reformer, which is a reactor; in other words, a content of a recycled material may be determined as appropriate.

For the purpose of recycling a low-boiling component, a known technique, e.g. appropriately providing a recycle line with a pressurization means can be employed.

According to this invention, a liquefied petroleum gas can be produced from a synthesis gas or a carbon-containing starting material such as a natural gas by utilizing an existing methanol production plant or an existing dimethyl ether production plant, and establishing an LPG production apparatus of this invention therewith.

EXAMPLES

The following will describe the present invention in more detail with reference to Examples. However, the present invention is not limited to these Examples.

Example 1

(Preparation of a Catalyst)

A mechanically powdered catalyst in which 0.5 wt % of Pd was supported on silica ($Pd/SiO_2$; average particle size: 1 μm) was used as a Pd- and/or Pt-based catalyst component. The catalyst was prepared as follows.

The silica, which is a support for the Pd- and/or Pt-based catalyst component, was CARIACT G3 (trade name), produced by Fuji Silysia Chemical Ltd. The silica had a specific surface area of 820 $m^2/g$, as determined by a BET method with $N_2$ as an adsorption gas, using ASAP2010 (Shimadzu Corporation).

First, the silica was pulverized to 20 to 40 mesh, sized and dried. And then, 8.8 mL of a 50 mg/mL aqueous solution of $Pd(NO_3)_2(NH_3)_2$ was added drop by drop to 20 g of the silica. After sufficiently impregnating the solution into pores, the silica was dried in a drying machine at 120° C. for 12 hours. The above process of impregnation and drying was repeated two more times.

Then, the silica impregnated with Pd was calcined at 450° C. in the air for 8 hours. Subsequently, it was mechanically pulverized to give a Pd- and/or Pt-based catalyst component.

A mechanically powdered proton-type USY zeolite with a $SiO_2/Al_2O_3$ ratio of 10, produced by Catalysts & Chemicals Industries Co., Ltd., (USY(10); average particle size: 1 μm) was used as a USY-type zeolite.

The Pd- and/or Pt-based catalyst component thus prepared and the USY-type zeolite were homogeneously mixed with $Pd/SiO_2:USY=1:2$ (by weight). And, the mixture was molded by a tablet-compression and sized to give a granular molded catalyst having an average particle size of 1 mm.

(Production of LPG)

In a tubular reactor with an inner diameter of 6 mm was placed 1 g of the catalyst prepared as described above, and the catalyst was reduced under a hydrogen stream at 400° C. for 2 hours before the beginning of the reaction.

After reduction treatment of the catalyst, a starting gas consisting of 75 mol % of hydrogen and 25 mol % of dimethyl ether ($H_2/DME=3$ (molar ratio)) was passed through the catalyst layer at a reaction temperature of 375° C., a reaction pressure of 2.1 MPa and a gas space velocity of 2000 $hr^{-1}$ (W/F=9.0 g·h/mol) to carry out the LPG production reaction.

Gas chromatographic analysis of the product indicated that, after three hours from the beginning of the reaction, a conversion of dimethyl ether was 100%, a conversion of dimethyl ether to carbon monoxide was 4.3%, a conversion of dimethyl ether to carbon dioxide was 0.0%, and a conversion of dimethyl ether to a hydrocarbon was 95.6%. The produced hydrocarbon gas contained propane and butane in 60.4% on the basis of carbon. A conversion of dimethyl ether to propane and butane was 57.7% on the basis of carbon.

The results are shown in Table 1.

Example 2

(Preparation of a Catalyst)

A catalyst was prepared in the same way as Example 1, except that a proton-type USY zeolite with a $SiO_2/Al_2O_3$ ratio of 20 (USY(20)) was used as a USY-type zeolite.

(Production of LPG)

Using the prepared catalyst, the LPG production reaction was carried out in the same way as Example 1.

Gas chromatographic analysis of the product indicated that, after three hours from the beginning of the reaction, a conversion of dimethyl ether was 100%, a conversion of dimethyl ether to carbon monoxide was 2.7%, a conversion of dimethyl ether to carbon dioxide was 0.0%, and a conversion of dimethyl ether to a hydrocarbon was 97.3%. The produced hydrocarbon gas contained propane and butane in 65.2% on the basis of carbon. A conversion of dimethyl ether to propane and butane was 63.4% on the basis of carbon.

The results are shown in Table 1.

Example 3

(Preparation of a Catalyst)

A catalyst was prepared in the same way as Example 1, except that a proton-type USY zeolite with a $SiO_2/Al_2O_3$ ratio of 30 (USY(30)) was used as a USY-type zeolite.

(Production of LPG)

Using the prepared catalyst, the LPG production reaction was carried out in the same way as Example 1.

Gas chromatographic analysis of the product indicated that, after three hours from the beginning of the reaction, a conversion of dimethyl ether was 99.8%, a conversion of dimethyl ether to carbon monoxide was 2.7%, a conversion of dimethyl ether to carbon dioxide was 0.0%, and a conversion of dimethyl ether to a hydrocarbon was 97.1%. The produced hydrocarbon gas contained propane and butane in 64.3% on the basis of carbon. A conversion of dimethyl ether to propane and butane was 62.4% on the basis of carbon.

The results are shown in Table 1.

dimethyl ether to carbon dioxide was 0.0%, and a conversion of dimethyl ether to a hydrocarbon was 96.9%. The produced hydrocarbon gas contained propane and butane in 61.5% on the basis of carbon. A conversion of dimethyl ether to propane and butane was 59.6% on the basis of carbon.

The results are shown in Table 2. For comparison, the results of Example 2 are also shown in Table 2.

TABLE 2

|  | Example 2 | Example 4 |
|---|---|---|
| Catalyst | $Pd/SiO_2$:USY(20) = 1:2 | $Pd/SiO_2$:USY(20) = 1:1 |
| DME conversion (%) | 100.0 | 99.8 |
| CO yield (%) | 2.7 | 3.0 |
| $CO_2$ yield (%) | 0.0 | 0.0 |
| Hydrocarbon yield (%) | 97.3 | 96.9 |
| Product composition (%) |  |  |
| C1 (methane) | 3.2 | 1.7 |
| C2 (ethane) | 12.2 | 15.0 |
| C3 (propane) | 25.6 | 25.4 |
| C4 (butane) | 39.5 | 36.1 |
| C5 (pentane) | 12.8 | 15.1 |
| C6 (hexane) | 6.6 | 6.7 |
| C3 + C4 | 65.2 | 61.5 |
| C3 + C4 yield (%) | 63.4 | 59.6 |

Example 5

(Preparation of a Catalyst)

A catalyst was prepared in the same way as Example 4, except that CARIACT Q6 (trade name), produced by Fuji Silysia Chemical Ltd., was used as a silica, which is a support

TABLE 1

|  | Example 1 | Example 2 | Example 3 |
|---|---|---|---|
| Catalyst | $Pd/SiO_2$:USY(10) = 1:2 | $Pd/SiO_2$:USY(20) = 1:2 | $Pd/SiO_2$:USY(30) = 1:2 |
| DME conversion (%) | 100.0 | 100.0 | 99.8 |
| CO yield (%) | 4.3 | 2.7 | 2.7 |
| $CO_2$ yield (%) | 0.0 | 0.0 | 0.0 |
| Hydrocarbon yield (%) | 95.6 | 97.3 | 97.1 |
| Product composition (%) |  |  |  |
| C1 (methane) | 2.0 | 3.2 | 4.5 |
| C2 (ethane) | 15.4 | 12.2 | 11.1 |
| C3 (propane) | 25.4 | 25.6 | 24.5 |
| C4 (butane) | 35.0 | 39.5 | 39.8 |
| C5 (pentane) | 15.1 | 12.8 | 12.9 |
| C6 (hexane) | 7.2 | 6.6 | 7.0 |
| C3 + C4 | 60.4 | 65.2 | 64.3 |
| C3 + C4 yield (%) | 57.7 | 63.4 | 62.4 |

Example 4

(Preparation of a Catalyst)

A catalyst was prepared in the same way as Example 2, except that the $Pd/SiO_2$ and the USY-type zeolite were homogeneously mixed with $Pd/SiO_2$:USY(20)=1:1 (by weight).

(Production of LPG)

Using the prepared catalyst, the LPG production reaction was carried out in the same way as Example 1.

Gas chromatographic analysis of the product indicated that, after three hours from the beginning of the reaction, a conversion of dimethyl ether was 99.8%, a conversion of dimethyl ether to carbon monoxide was 3.0%, a conversion of for a Pd- and/or Pt-based catalyst component. The silica had a specific surface area of 450 $m^2/g$, as determined by a BET method with $N_2$ as an adsorption gas, using ASAP2010 (Shimadzu Corporation).

(Production of LPG)

Using the prepared catalyst, the LPG production reaction was carried out in the same way as Example 1.

Gas chromatographic analysis of the product indicated that, after three hours from the beginning of the reaction, a conversion of dimethyl ether was 99.4%, a conversion of dimethyl ether to carbon monoxide was 1.2%, a conversion of dimethyl ether to carbon dioxide was 0.1%, and a conversion of dimethyl ether to a hydrocarbon was 98.2%. The produced hydrocarbon gas contained propane and butane in 66.0% on the basis of carbon. A conversion of dimethyl ether to propane and butane was 64.8% on the basis of carbon.

The results are shown in Table 3.

Example 6

(Preparation of a Catalyst)

A catalyst was prepared in the same way as Example 5, except that the $Pd/SiO_2$ having an average particle size of 1 mm and the USY-type zeolite (USY(20)) having an average particle size of 1 mm were homogeneously mixed.

(Production of LPG)

Using the prepared catalyst, the LPG production reaction was carried out in the same way as Example 1.

Gas chromatographic analysis of the product indicated that, after three hours from the beginning of the reaction, a conversion of dimethyl ether was 97.3%, a conversion of dimethyl ether to carbon monoxide was 2.4%, a conversion of dimethyl ether to carbon dioxide was 0.1%, and a conversion of dimethyl ether to a hydrocarbon was 94.7%. The produced hydrocarbon gas contained propane and butane in 53.4% on the basis of carbon. A conversion of dimethyl ether to propane and butane was 50.6% on the basis of carbon.

The results are shown in Table 3.

TABLE 3

|  | Example 5 | Example 6 |
|---|---|---|
| Catalyst | $Pd/SiO_2$:USY(20) = 1:1 | $Pd/SiO_2$:USY(20) = 1:1 |
| Average particle size of a catalyst component | 1 μm | 1 mm |
| DME conversion (%) | 99.4 | 97.3 |
| CO yield (%) | 1.2 | 2.4 |
| $CO_2$ yield (%) | 0.1 | 0.1 |
| Hydrocarbon yield (%) | 98.2 | 94.7 |
| Product composition (%) |  |  |
| C1 (methane) | 3.2 | 2.3 |
| C2 (ethane) | 12.7 | 14.5 |
| C3 (propane) | 25.6 | 21.1 |
| C4 (butane) | 40.4 | 32.3 |
| C5 (pentane) | 12.9 | 16.2 |
| C6 (hexane) | 5.2 | 13.6 |
| C3 + C4 | 66.0 | 53.4 |
| C3 + C4 yield (%) | 64.8 | 50.6 |

Comparative Example 1

(Preparation of a Catalyst)

A mechanically powdered Cu—Zn-based methanol synthesis catalyst, C79 produced by Sud Chemie Japan, Inc., (also referred to as "Cu—Zn") and a mechanically powdered proton-type USY zeolite with a $SiO_2/Al_2O_3$ ratio of 12.2, produced by Catalysts & Chemicals Industries Co., Ltd., (also referred to as "USY") were homogeneously mixed with Cu—Zn:USY=1:1 (by weight). And, the mixture was molded by a tablet-compression and sized to give a granular catalyst for producing a liquefied petroleum gas having an average particle size of 1 mm.

(Production of LPG)

Using the prepared catalyst, the LPG production reaction was carried out in the same way as Example 1, except that a reaction temperature was 340° C.

Gas chromatographic analysis of the product indicated that, after three hours from the beginning of the reaction, a conversion of dimethyl ether was 99.9%, a conversion of dimethyl ether to carbon monoxide was 15.0%, a conversion of dimethyl ether to carbon dioxide was 16.0%, and a conversion of dimethyl ether to a hydrocarbon was 68.9%. The produced hydrocarbon gas contained propane and butane in 75.5% on the basis of carbon. A conversion of dimethyl ether to propane and butane was 52.0% on the basis of carbon.

The results are shown in Table 4.

Comparative Example 2

(Preparation of a Catalyst)

A catalyst was prepared in the same way as Example 1, except that a proton-type ZSM-5 with a $SiO_2/Al_2O_3$ ratio of 40 was used instead of a USY-type zeolite.

(Production of LPG)

Using the prepared catalyst, the LPG production reaction was carried out in the same way as Example 1.

Gas chromatographic analysis of the product indicated that, after three hours from the beginning of the reaction, a conversion of dimethyl ether was 100%, a conversion of dimethyl ether to carbon monoxide was 8.7%, a conversion of dimethyl ether to carbon dioxide was 0.1%, and a conversion of dimethyl ether to a hydrocarbon was 91.1%. The produced hydrocarbon gas contained propane and butane in 52.0% on the basis of carbon. A conversion of dimethyl ether to propane and butane was 47.4% on the basis of carbon.

The results are shown in Table 4.

Comparative Example 3

(Preparation of a Catalyst)

A 0.5 wt % Pd-supported proton-type ZSM-5 with a $SiO_2/Al_2O_3$ ratio of 40, produced by Tosoh Corporation, was used as a catalyst. The catalyst was prepared as follows.

First, 0.0825 g of palladium chloride (purity: >99 wt %) was dissolved in 10 mL of a 12.5 wt % aqueous ammonia solution at 40 to 50° C. And then, 150 mL of ion-exchanged water was added to the resulting solution to obtain a Pd-containing solution. 10 g of ZSM-5 zeolite was added to the obtained Pd-containing solution, and the mixture was heated and stirred at 60 to 70° C. for 6 hours. After the ion-exchange process, the resulting material was repeatedly filtrated and washed with ion-exchanged water until no chloride ions were observed in a filtrate.

Then, the Pd ion-exchanged ZSM-5 was dried at 120° C. for 12 hours, and calcined at 500° C. in an air for 2 hours. Subsequently, it was mechanically pulverized, and then molded by a tablet-compression and sized to give a granular catalyst for producing a liquefied petroleum gas (Pd-ZSM-5) having an average particle size of 1 mm.

(Production of LPG)

Using the prepared catalyst, the LPG production reaction was carried out in the same way as Example 1, except that a reaction temperature was 350° C.

Gas chromatographic analysis of the product indicated that, after three hours from the beginning of the reaction, a conversion of dimethyl ether was 100%, a conversion of dimethyl ether to carbon monoxide was 1.4%, a conversion of dimethyl ether to carbon dioxide was 0.4%, and a conversion of dimethyl ether to a hydrocarbon was 98.2%. The produced hydrocarbon gas contained propane and butane in 50.6% on the basis of carbon. A conversion of dimethyl ether to propane and butane was 49.7% on the basis of carbon.

The results are shown in Table 4.

Comparative Example 4

(Preparation of a Catalyst)

A catalyst (Pd-USY(20); the amount of supported Pd: 0.5 wt %) was prepared in the same way as Comparative Example 3, except that a proton-type USY zeolite with a $SiO_2/Al_2O_3$ ratio of 20 (USY(20)) was used instead of a proton-type ZSM-5.

(Production of LPG)

Using the prepared catalyst, the LPG production reaction was carried out in the same way as Example 1, except that a reaction temperature was 350° C.

Gas chromatographic analysis of the product indicated that, after three hours from the beginning of the reaction, a conversion of dimethyl ether was 89.5%, a conversion of dimethyl ether to carbon monoxide was 14.9%, a conversion of dimethyl ether to carbon dioxide was 0.2%, and a conversion of dimethyl ether to a hydrocarbon was 74.4%. The produced hydrocarbon gas contained propane and butane in 2.6% on the basis of carbon. A conversion of dimethyl ether to propane and butane was 1.9% on the basis of carbon.

The results are shown in Table 4.

TABLE 4

|  | Comp. Exam. 1 | Comp. Exam. 2 | Comp. Exam. 3 | Comp. Exam. 4 |
|---|---|---|---|---|
| Catalyst | Cu—Zn USY | Pd/SiO$_2$ ZSM-5 | Pd-ZSM-5 | Pd-USY(20) |
| DME conversion (%) | 99.9 | 100.0 | 100.0 | 89.5 |
| CO yield (%) | 15.0 | 8.7 | 1.4 | 14.9 |
| CO$_2$ yield (%) | 16.0 | 0.1 | 0.4 | 0.2 |
| Hydrocarbon yield (%) | 68.9 | 91.1 | 98.2 | 74.4 |
| Product composition (%) |  |  |  |  |
| C1 (methane) | 4.4 | 14.3 | 1.8 | 94.9 |
| C2 (ethane) | 5.1 | 19.4 | 29.2 | 0.8 |
| C3 (propane) | 19.7 | 38.2 | 33.4 | 2.0 |
| C4 (butane) | 55.8 | 13.8 | 17.3 | 0.6 |
| C5 (pentane) | 10.9 | 7.0 | 11.3 | 0.3 |
| C6 (hexane) | 4.1 | 7.2 | 7.2 | 1.4 |
| C3 + C4 | 75.5 | 52.0 | 50.6 | 2.6 |
| C3 + C4 yield (%) | 52.0 | 47.4 | 49.7 | 1.9 |

INDUSTRIAL APPLICABILITY

As described above, a hydrocarbon containing propane or butane as a main component, i.e. a liquefied petroleum gas (LPG), can be economically produced with high activity, high selectivity and high yield from at least one of methanol and dimethyl ether by using a catalyst for producing a liquefied petroleum gas according to the present invention.

Furthermore, according to the present invention, a liquefied petroleum gas containing propane or butane as a main component can be economically produced from a carbon-containing starting material such as a natural gas, or from a synthesis gas.

What is claimed is:

1. A process for producing a liquefied petroleum gas, comprising a step of:
    reacting at least one reactant selected from the group consisting of methanol and dimethyl ether with hydrogen in the presence of a catalyst, whereby producing a liquefied petroleum gas containing propane or butane as a main component,
    wherein the catalyst comprises a Pd- and/or Pt-based catalyst component in which Pd and/or Pt is supported on a support and a USY-type zeolite.

2. A process for producing a liquefied petroleum gas according to claim 1, further comprising producing methanol by passing a synthesis gas through a catalyst layer comprising a methanol synthesis catalyst, thereby producing a reactant gas containing methanol and hydrogen; wherein the methanol in the reactant gas produced in the step of producing methanol is used as the reactant.

3. A process for producing a liquefied petroleum gas according to claim 1, further comprising producing dimethyl ether by passing a synthesis gas through a catalyst layer comprising a methanol synthesis catalyst and a methanol dehydration catalyst, thereby producing a reactant gas containing dimethyl ether and hydrogen; wherein the dimethyl ether in the reactant gas produced in the step of producing dimethyl ether is used as the reactant.

4. A process for producing a liquefied petroleum gas according to claim 1, further comprising
    (1) producing a synthesis gas from a carbon-containing starting material and at least one selected from the group consisting of H$_2$O, O$_2$ and CO$_2$; and
    (2) producing methanol wherein the synthesis gas is passed through a catalyst layer comprising a methanol synthesis catalyst, thereby producing a reactant gas containing methanol and hydrogen;
    wherein the methanol in the reactant gas produced in the step of producing methanol is used as the reactant.

5. A process for producing a liquefied petroleum gas according to claim 1, further comprising
    (1) producing a synthesis gas from a carbon-containing starting material and at least one selected from the group consisting of H$_2$O, O$_2$ and CO$_2$; and
    (2) producing dimethyl ether wherein the synthesis gas is passed through a catalyst layer comprising a methanol synthesis catalyst and a methanol dehydration catalyst, thereby producing a reactant gas containing dimethyl ether and hydrogen;
    wherein the dimethyl ether in the reactant gas produced in the step of producing dimethyl ether is used as the reactant.

6. A process according to claim 1, wherein a ratio (by weight) of the Pd- and/or Pt-based catalyst component to the USY-type zeolite is 0.1 to 1.5 (Pd-and/or Pt-based catalyst component/USY-type zeolite).

7. A process according to claim 1, wherein the amount of supported Pd and/or Pt in the Pd- and/or Pt-based catalyst component is 0.1 to 5% by weight.

8. A process according to claim 7, wherein the support for the Pd- and/or Pt-based catalyst component is silica.

9. A process according to claim 8, wherein a specific surface area of the silica support for the Pd- and/or Pt-based catalyst component is 450 m$^2$/g or more.

10. A process according to claim 1, wherein the USY-type zeolite has a SiO$_2$/Al$_2$O$_3$ ratio of 5 to 50.

* * * * *